(12) United States Patent
Rock et al.

(10) Patent No.: US 6,768,011 B2
(45) Date of Patent: Jul. 27, 2004

(54) METHOD FOR THE PREPARATION OF CITALOPRAM

(75) Inventors: Michael Harold Rock, Hvidovre (DK); Haleh Ahmadian, Solrød Strand (DK)

(73) Assignee: H. Lundbeck A/S, Valby-Copenhagen (DK)

( * ) Notice: Subject to any disclaimer, the term of this patent is extended or adjusted under 35 U.S.C. 154(b) by 0 days.

(21) Appl. No.: 10/232,994

(22) Filed: Aug. 29, 2002

(65) Prior Publication Data

US 2003/0092761 A1 May 15, 2003

Related U.S. Application Data

(63) Continuation of application No. PCT/DK01/00140, filed on Mar. 1, 2001.

(30) Foreign Application Priority Data

Mar. 3, 2000 (DK) .......................................... 2000 00353

(51) Int. Cl.[7] ........................ C07D 307/98; A61K 31/34
(52) U.S. Cl. ....................................... 549/467; 514/469
(58) Field of Search ......................................... 549/467

(56) References Cited

U.S. PATENT DOCUMENTS

| | | | |
|---|---|---|---|
| 3,467,675 A | 9/1969 | Petersen et al. | 260/346.2 |
| 4,136,193 A | 1/1979 | Bogeso et al. | 424/285 |
| 4,650,884 A | 3/1987 | Bogeso | 549/467 |
| 4,943,590 A | 7/1990 | Boegesoe et al. | 514/469 |
| 5,296,507 A | 3/1994 | Tanaka et al. | 514/465 |
| 6,020,501 A | 2/2000 | Massonne et al. | 549/307 |
| 6,028,204 A | 2/2000 | Massonne et al. | 549/307 |
| 6,229,026 B1 | 5/2001 | Petersen | 549/467 |
| 6,258,842 B1 | 7/2001 | Petersen et al. | 514/469 |
| 6,291,689 B1 | 9/2001 | Petersen et al. | 549/467 |
| 6,310,222 B1 | 10/2001 | Ikemoto et al. | 549/467 |
| 6,365,747 B1 | 4/2002 | Dall'Asta et al. | 548/146 |
| 6,392,060 B2 | 5/2002 | Petersen et al. | 549/307 |
| 6,403,813 B1 | 6/2002 | Petersen et al. | 549/305 |
| 6,407,267 B1 | 6/2002 | Rock et al. | 549/467 |

(List continued on next page.)

FOREIGN PATENT DOCUMENTS

| | | |
|---|---|---|
| WO | 98/19511 | 5/1998 |
| WO | 98/19512 | 5/1998 |
| WO | 98/19513 | 5/1998 |

(List continued on next page.)

OTHER PUBLICATIONS

U.S. patent application Ser. No. 10/183,958, filed Jun. 25, 2002.
U.S. patent application Ser. No. 10/291,174 filed Nov. 8, 2002.

(List continued on next page.)

*Primary Examiner*—Rita Desai
*Assistant Examiner*—Raymond Covington
(74) *Attorney, Agent, or Firm*—Darby & Darby

(57) ABSTRACT

The invention relates to a method for the preparation of citalopram comprising reaction of a compound of formula II

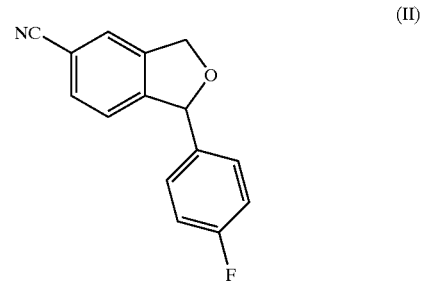

(II)

with a compound having the formula

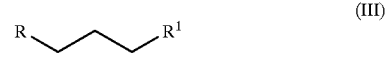

(III)

wherein R is halogen or —O—SO$_2$—X, wherein X is alkyl, alkenyl, alkynyl or optionally alkyl substituted aryl or aralkyl, and R$^1$ is dimethylamino, halogen, —O—SO$_2$—X wherein X is as defined above, provided that R is not halogen when R$^1$ is dimethylamino;

and if R$^1$ is dimethylamino followed by isolation of citalopram base or a pharmaceutically acceptable acid addition salt thereof, and if R$^1$ is halogen or —O—SO$_2$—X, wherein X is as defined above, followed by conversion of the resulting compound of formula

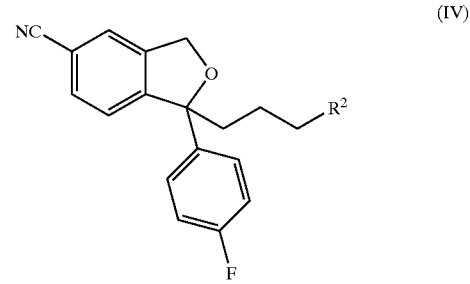

(IV)

wherein R$^2$ is halogen or a group of formula —O—SO$_2$—X wherein X is as defined above to citalopram, followed by isolation of citalopram base or a pharmaceutically acceptable acid addition salt thereof.

5 Claims, No Drawings

U.S. PATENT DOCUMENTS

| | | | |
|---|---|---|---|
| 6,420,574 B2 * | 7/2002 | Petersen et al. | 549/467 |
| 6,426,422 B1 | 7/2002 | Petersen et al. | 549/467 |
| 6,433,196 B1 | 8/2002 | Ikemoto et al. | 549/469 |
| 6,441,201 B1 | 8/2002 | Weber | 549/468 |
| 6,455,710 B1 | 9/2002 | Villa et al. | 549/462 |
| 6,458,973 B1 | 10/2002 | Dall'Asta et al. | 549/305 |
| 6,509,483 B2 | 1/2003 | Petersen et al. | 549/467 |
| 2002/0004604 A1 | 1/2002 | Petersen et al. | 549/462 |
| 2002/0035277 A1 | 3/2002 | Rock et al. | 549/467 |
| 2002/0040153 A1 | 4/2002 | Petersen | 549/467 |
| 2002/0061925 A1 | 5/2002 | Petersen et al. | 514/469 |
| 2002/0077353 A1 | 6/2002 | Petersen et al. | 514/469 |
| 2002/0087012 A1 | 7/2002 | Castellin et al. | 549/467 |
| 2002/0128497 A1 | 9/2002 | Bolzonella et al. | 549/467 |
| 2002/0165403 A1 | 11/2002 | Petersen et al. | 549/467 |
| 2002/0198391 A1 | 12/2002 | Petersen et al. | 549/307 |
| 2003/0013895 A1 | 1/2003 | Petersen | 549/307 |

FOREIGN PATENT DOCUMENTS

| | | | |
|---|---|---|---|
| WO | 99/30548 | 6/1999 | |
| WO | 00/11926 | 3/2000 | |
| WO | 00/12044 | 3/2000 | |
| WO | 00/13648 | 3/2000 | |
| WO | 00/23431 | 4/2000 | C07D/307/87 |
| WO | 00/39112 | 7/2000 | C07D/307/87 |
| WO | 00/44738 | 8/2000 | C07D/307/88 |
| WO | 01/02383 | 1/2001 | C07D/307/87 |
| WO | 01/45483 | 6/2001 | |
| WO | 01/47877 | 7/2001 | |
| WO | 01/47909 | 7/2001 | C07D/307/87 |
| WO | 01/49672 | 7/2001 | C07D/307/87 |
| WO | 01/51477 | 7/2001 | C07D/307/87 |
| WO | 01/51478 | 7/2001 | C07D/307/87 |
| WO | 01/62754 | 8/2001 | C07D/307/87 |
| WO | 01/66536 | 9/2001 | C07D/307/87 |
| WO | 01/68627 | 9/2001 | C07D/307/87 |
| WO | 01/68628 | 9/2001 | C07D/307/87 |
| WO | 01/68629 | 9/2001 | C07D/307/87 |
| WO | 01/68630 | 9/2001 | C07D/307/87 |
| WO | 01/68631 | 9/2001 | C07D/307/87 |
| WO | 01/68632 | 9/2001 | C07D/307/87 |
| WO | 01/85712 | 11/2001 | C07D/307/87 |
| WO | 02/04435 | 1/2002 | C07D/307/87 |

OTHER PUBLICATIONS

U.S. patent application Ser. No. 10/233,132, filed Aug. 30, 2002.

U.S. patent application Ser. No. 10/237,145, filed Sep. 5, 2002.

U.S. patent application Ser. No. 10/238,907, filed Sep. 6, 2002.

U.S. patent application Ser. No. 10/228,388, filed Aug. 23, 2002.

U.S. patent application Ser. No. 10/238,843, filed Sep. 9, 2002.

U.S. patent application Ser. No. 10/245,824, filed Sep. 12, 2002.

U.S. patent application Ser. No. 10/242,804, filed Sep. 10, 2002.

U.S. patent application Ser. No. 10/291,174, filed Nov. 8, 2002.

Levy, L.F., "4–Aminophthalide and Some Derivatives", *J. Chem. Soc.* pp. 867–870 (1931).

Tirouflet, Jean, "Phtalide Substitués en 5", *Bull. Soc. Sci. de Bretagne* 26:34–43 (1951).

Forney, LeRoy S.., "Reaction of Terephthalic Acid with Formaldehyde in Sulfur Trioxide Media," *J. Org. Chem* 35:1695–1696 (1970).

Dordor, Isabelle M. et al., "Reaction of Oxazolines with Phosphorus Oxychloride," *Tetrahedron Letters* 24:1437–1440 (1983).

Barton, Sir Derek et al., *Comprehensive Organic Chemistry. The Synthesis and Reactions of Organic Compounds,* vol. 2, pp. 1024–1025.

Bigler, Allan et al., "Quantitative Structure–activity Relationships in a Series of Selective 5–HHT uptake inhibitors, "*Eur. J. Med. Chem.* 3:289–295 (1997).

* cited by examiner

METHOD FOR THE PREPARATION OF CITALOPRAM

This application is a continuation of International application no. PCT/DK01/00140, filed Mar. 1, 2001. The prior application is hereby incorporated by reference in its entirety.

The present invention relates to a method for the preparation of the well-known antidepressant drug citalopram, 1-[3-(dimethylamino)propyl]-1-(4-fluorophenyl)-1,3-dihydro-5-isobenzofurancarbonitrile.

BACKGROUND OF THE INVENTION

Citalopram is a well-known antidepressant drug that has now been on the market for some years and has the following structure:

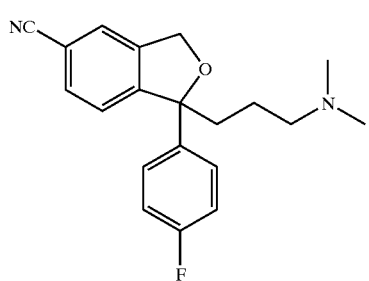

(I)

It is a selective, centrally acting serotonin (5-hydroxytryptamine; 5-HT) reuptake inhibitor, accordingly having antidepressant activities. The antidepressant activity of the compound has been reported in several publications, eg. J. Hyttel. *Prog. Neuro-Psychopharmacol. & Biol. Psychiat.* 1982, 6, 277–295 and A. Gravem *Acta Psychiatr. Scand.* 1987, 75, 478–486. The compound has further been disclosed to show effects in the treatment of dementia and cerebrovascular disorders, EP-A-474580.

Citalopram was first disclosed in DE 2,657,013, corresponding to U.S. Pat. No. 4,136,193. This patent publication describes the preparation of citalopram by one method and outlines a further method which may be used for preparing citalopram.

According to the process described, the corresponding 1-(4-fluorophenyl)-1,3-dihydro-5-isobenzofurancarbonitrile is reacted with 3-(N,N-dimethylamino)propyl-chloride in the presence of methylsulfinylmethide as condensing agent. The starting material was prepared from the corresponding 5-bromo derivative by reaction with cuprous cyanide.

International patent application No. WO 98/019511 discloses a process for the manufacture of citalopram wherein a (4-(cyano, alkyloxycarbonyl or alkylaminocarbonyl)-2-hydroxymethylphenyl-(4-fluorophenyl)methanol compound is subjected to ring closure. The resulting 5-(alkyloxycarbonyl or alkylaminocarbonyl)-1-(4-fluorophenyl)-1,3-dihydroisobenzofuran is converted to the corresponding 5-cyano derivative and the 5-cyano derivative is then alkylated with a (3-dimethylamino) propylhalogenide in order to obtain citalopram.

It has now, surprisingly, been found that citalopram may be manufactured by a novel favourable process.

The alkylation process according to the invention is particularly advantageous because the formation of by-products by polymerisation of the alkylating agent is avoided whereby a reduction in the amount of alkylating reagent to be used is made possible. The process of the invention also provides high yields.

SUMMARY OF THE INVENTION

Accordingly, the present invention relates to a method for the preparation of citalopram comprising reaction of a compound of formula

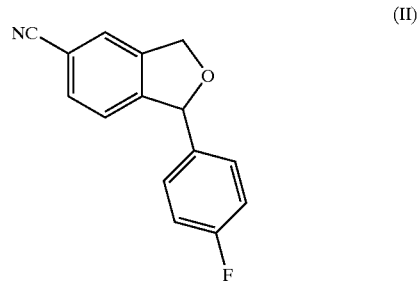

(II)

with a compound having the formula

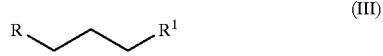

(III)

wherein R is halogen or —O—SO$_2$—X wherein X is alkyl, alkenyl, alkynyl or optionally alkyl substituted aryl or aralkyl and R$^1$ is dimethylamino, halogen or —O—SO$_2$—X wherein X is as defined above, provided that R is not halogen when R$^1$ is dimethylamino;

and if R$^1$ is dimethylamino followed by isolation of citalopram base or a pharmaceutically acceptable acid addition salt thereof, and if R$^1$ is halogen or —O—SO$_2$-X wherein X is as defined above, followed by conversion of the resulting compound of formula

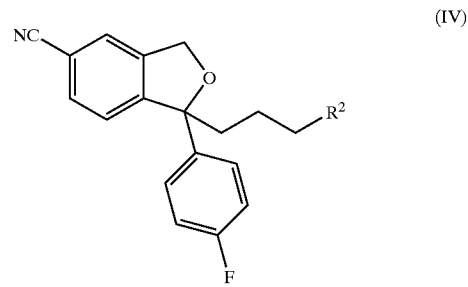

(IV)

wherein R$^2$ is halogen or a group of formula —O—SO$_2$—X, wherein X is as defined above, to citalopram, followed by isolation of citalopram base or a pharmaceutically acceptable acid addition salt thereof.

Thus in one embodiment, the present invention relates to a method where a compound of formula (II) is reacted with a compound of formula (III) wherein R is —O—SO$_2$—X wherein X is as defined above and R$^1$ is dimethylamino resulting in the direct formation of citalopram.

In a second embodiment, the present invention relates to a method where a compound of formula (II) is reacted with a compound of formula (III) wherein R and R$^1$ are independently selected from halogen and —O—SO$_2$—X. The resulting compound of formula (IV) wherein R$^2$ is halogen or a group of formula —O—SO$_2$—X, where X is as defined above, is then converted to citalopram by reaction with a) dimethylamine or a metal salt thereof, b) methylamine followed by reductive amination, or c) an azide followed by reduction to form the corresponding amino compound and thereafter methylation or reductive amination.

In another aspect, the present invention provides the novel intermediates of the general formula (IV).

In yet another aspect, the present invention relates to an antidepressant pharmaceutical composition comprising citalopram manufactured by the process of the invention.

The alkylation step where the compound of formula (II) is reacted with a compound of formula (III) is suitably carried out by treatment of the compound of formula (II) with a base such as for example LDA (lithium diisopropylamine), LiHMDS (lithium hexamethyldisilazane), NaH, NaHMDS (sodium hexamethyldisilazane), or metalalkoxides such as NaOMe, KOMe, LiOMe, NaOtertBu, KOtertBu and LiOtertBu in an aprotic organic solvent such as THF (tetrahydrofuran), DMF (dimethylformamide), NMP (N-methylpyrrolidon), ethers such as diethylether, or dioxalane, toluene, benzene or alkanes and mixtures thereof. The anion formed is then reacted with a compound of formula (III) whereby a group of formula —$CH_2$—$CH_2$—$CH_2$—$R^2$ or a group of formula —$CH_2$—$CH_2$—$CH_2$—$N(CH_3)_2$ is introduced into position 1 of the isobenzofuranyl ring system.

The compound of formula (IV) is then reacted with dimethylamine or a metal salt thereof, such as $M^+$, —$N(CH_3)_2$ wherein $M^+$ is $Li^+$ or $Na^+$. The reaction is suitably carried out in an aprotic organic solvent such as THF (tetrahydrofuran), DMF (dimethylformamide), NMP (N-methyl pyrrolidon), ethers such as diethylether, or dioxalane, toluene, benzene, or alkanes and mixtures thereof. The compound of formula (IV) may also be converted to citalopram by reaction with dimethylammonium chloride.

The reaction conditions, solvents, etc. used for the reactions described above are conventional conditions for such reactions and may easily be determined by a person skilled in the art.

Alternatively, the compound of formula (IV) is reacted with an azide, such as sodium azide, followed by reduction, using e.g. Pd/C as a catalyst, to form the corresponding amine of formula

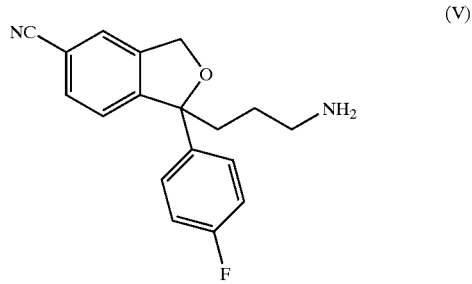

(V)

and thereafter methylation or reductive amination to form citalopram.

The compound of formula (IV) may also be converted to citalopram by reaction with methylamine to form a compound of formula

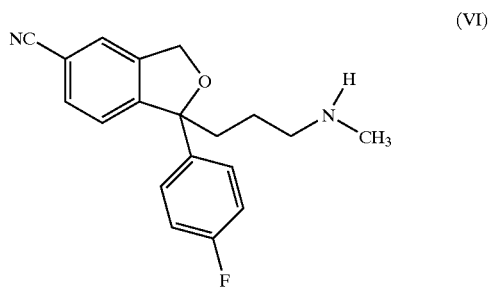

(VI)

followed by methylation or reductive amination to form citalopram.

The amino groups in the compounds of formula (V) and (VI) may be methylated with methylating agents such as MeI and $Me_2SO_4$ wherein Me is methyl. The methylation is carried out using conventional procedures for carrying out such reactions.

Methyl groups may also be introduced into the compounds of formula (V) or (VI) by reductive amination. According to this procedure, the compounds of formula (V) or (VI) are reacted with compounds such as formaldehyde, paraformaldehyde or trioxan in presence of a reducing agent such as $NaBH_4$ or $NaBH_3CN$. The reductive amination is carried out using conventional procedures for carrying out such reactions.

The starting material of formula (II) may be prepared as described in U.S. Pat. No. 4,136,193 or as described in WO 98/019511.

The compounds of formula (III) are known or may be prepared from known compounds using conventional methods.

Citalopram is on the market as an antidepressant drug in the form of the racemate. However, in the near future, the active S-enantiomer of citalopram is also going to be introduced to the market.

S-citalopram may be prepared by separation of the optically active isomers by chromatography.

Throughout the specification and claims, the term alkyl refers to a branched or unbranched alkyl group having from one to six carbon atoms inclusive, such as methyl, ethyl, 1-propyl, 2-propyl, 1-butyl, 2-butyl, 2-methyl-2-propyl, 2,2-dimethyl-1-ethyl and 2-methyl-1-propyl.

Similarly, alkenyl and alkynyl, respectively, designate such groups having from two to six carbon atoms, including one double bond or triple bond respectively, such as ethenyl, propenyl, butenyl, ethynyl, propynyl and butynyl.

The term aryl refers to a mono- or bicyclic carbocyclic aromatic group, such as phenyl and naphthyl, in particular phenyl.

The term aralkyl refers to aryl-alkyl, wherein aryl and alkyl is as defined above.

Optionally, alkyl substituted aryl and aralkyl refers to aryl and aralkyl groups, which may optionally be substituted with one or more alkyl groups.

Halogen means chloro, bromo or iodo.

The compound of general Formula I may be used as the free base, in particular as citalopram base in crystalline form, or as a pharmaceutically acceptable acid addition salt thereof. As acid addition salts, such salts formed with organic or inorganic acids may be used. Exemplary of such organic salts are those with maleic, fumaric, benzoic, ascorbic, succinic, oxalic, bismethylenesalicylic, methanesulfonic, ethanedisulfonic, acetic, propionic, tartaric, salicylic, citric, gluconic, lactic, malic, mandelic, cinnamic, citraconic, aspartic, stearic, palmitic, itaconic, glycolic, p-aminobenzoic, glutamic, benzene sulfonic and theophylline acetic acids, as well as the 8-halotheophyllines, for example 8-bromotheophylline. Exemplary of such inorganic salts are those with hydrochloric, hydrobromic, sulfuric, sulfamic, phosphoric and nitric acids.

The acid addition salts of the compounds may be prepared by methods known in the art. The base is reacted with either the calculated amount of acid in a water miscible solvent, such as acetone or ethanol, with subsequent isolation of the salt by concentration and cooling, or with an excess of the acid in a water immiscible solvent, such as ethylether, ethylacetate or dichloromethane, with the salt separating spontaneously.

The pharmaceutical compositions of the invention may be administered in any suitable way and in any suitable form, for example orally in the form of tablets, capsules, powders or syrups, or parenterally in the form of usual sterile solutions for injection.

The pharmaceutical formulations of the invention may be prepared by conventional methods in the art. For example, tablets may be prepared by mixing the active ingredient with ordinary adjuvants and/or diluents and subsequently compressing the mixture in a conventional tabletting machine. Examples of adjuvants or diluents comprise: Corn starch, potato starch, talcum, magnesium stearate, gelatine, lactose, gums, and the like. Any other adjuvant or additive, colourings, aroma, preservatives etc. may be used provided that they are compatible with the active ingredients.

Solutions for injections may be prepared by dissolving the active ingredient and possible additives in a part of the solvent for injection, preferably sterile water, adjusting the solution to the desired volume, sterilising the solution and filling it in suitable ampoules or vials. Any suitable additive conventionally used in the art may be added, such as tonicity agents, preservatives, antioxidants, etc.

The invention is further illustrated by the following examples.

EXAMPLE 1

A solution of 1-(4-fluorophenyl)-1,3-dihydroisobenzofuran-5-carbonitrile (4.8 g, 0.02 mol) in THF(50 ml) was added dropwise to a solution of LDA (butyl lithium 1.6 M (15 mL), diisopropylamine (2.6 g )) at −30° C. under an atmosphere of nitrogen. After stirring at −30° C. for 10 minutes a solution of the alkyl halide/sulphonate (0.02 mol) in THF (25 mL) was added dropwise and allowed to warm to room temperature and stirred for a further 60 minutes. The reaction was then quenched with ice, extracted with toluene (3×50 mL), washed with water (50 mL) and concentrated under reduced pressure. The residue was purified by chromatography on silica gel using mixtures of n-heptane/EtOAc as the eluent. The resulting anion is then reacted with a compound of formula (III).

EXAMPLE 2

Preparation of 1-[3-(N,N-dimethylamino)propyl]-1-(4-fluorophenyl)-1,3-dihydro-5-isobenzofuran-carbonitrile (Citalopram, Oxalate):

To a solution of 1-(4-fluorophenyl)-1-[(3-p-toluenesulfonyloxy)propyl]-1,3-dihydro-5-isobenzo-furancarbonitrile (0.20 g, 0.4 mmol) in DMF (10 mL) was added triethylamine (1.4 mL, 7.0 mmol) and dimethylammonium chloride (0.41 g, 5.0 mmol). The reaction mixture was stirred at 70° C. overnight, then cooled to room temperature, poured into ice/$H_2O$ and extracted with $Et_2O$ (3×30 mL). The organic extracts were washed with $H_2O$ and brine, and evaporated. The residue was purified by silica gel chromatography (heptane, EtOAc, triethylamine 1:3:4%) and crystallised from acetone as the oxalate salt (0.12 g, 70%). DSC (open chamber), $T_{onset}$=158.96, $T_{peak}$=162.14.$^1$H NMR (DMSO-$d_6$) δ1.42 (1H, m); 1.51 (1H, m); 2.22 (2H, t, J=8.0 Hz); 2.62 (6H, s); 2.95 (2H, t, J=8.0 Hz); 5.15 (1H, d, J=14.0 Hz); 5.23 (1H, d, J=14.0 Hz); 7.18 (2H, t, J=9.0 Hz); 7.59 (2H, dd, J=5.0 and 8.0 Hz); 7.74 (1H, d, J=7.5 Hz); 7.79 (1H, d, J=7.0 Hz); 7.80 (1H, br s). $^{13}$C NMR (DMSO-$d_6$) δ19.3; 37.0; 42.3; 56.7; 71.2; 90.3; 110.7; 115.2; 115.3; 118.8; 123.2; 125.8; 127.0; 132.1; 139.9; 140.0; 148.161.4; 164.3. Anal. ($C_{20}H_{21}N_2O$, $C_2H_2O_4$) calcd. C: 63.76; H: 5.59; N: 6.76. Found C: 63.50; H: 5.78; N: 6.63.

EXAMPLE 3

Preparation of 1-[3-(N,N-dimethylamino)propyl]-1-(4-fluorophenyl)-1,3-dihydro-5-isobenzo-furancarbonitrile (Citalopram, Oxalate):

Dimethylamine (18 mL, 100 mmol, 33% in ethanol) was added to a solution of 1-(4-fluorophenyl)-1-[(3-methanesulfonyloxy)propyl]-1,3-dihydro-5-isobenzofurancarbonitrile (1.0 g, 2.7 mmol) in ethanol (10 mL) and THF (20 mL). The resulting mixture was stirred at room temperature for 1 h and at 60° C. for 3 h. After cooling, the reaction mixture was evaporated. 1 M NaOH (70 mL) was added to the residue and extracted with $Et_2O$ (100 mL). The organic extract was washed with brine, dried and evaporated. The residue was filtered through silica gel (EtOAc, heptane, triethylamine 75:25:1) and crystallised from acetone as the oxalate salt (0.72 g, 65%). DSC (open chamber), $T_{onset}$=158.56, $T_{peak}$=161.59. The NMR-spectra were identical with those obtained from citalopram oxalate prepared in example 2. Anal. ($C_{20}H_{21}N_2O$, $C_2H_2O_4$) calcd. C: 63.76; H: 5.59; N: 6.76. Found C: 63.57; H: 5.51; N: 6.77.

EXAMPLE 4

Preparation of 1-(3-Azidopropyl)-1-(4-fluorophenyl)-1,3-dihydro-5-isobenzofurancarbonitrile:

Sodium azide (5.5 g, 80.5 mmol) was added to a solution of 1-(4-fluorophenyl)-1-[(3-methanesulfo-nyloxy)propyl]-1,3-dihydro-5-isobenzofurancarbonitrile (4.0 g, 10.6 mmol) in DMF (100 mL). The resulting mixture was stirred at 40° C. for 3 h, and then refluxed for 2 h. After cooling the reaction mixture was poured into $H_2O$ and extracted with $Et_2O$ (4×200 mL). The organic extracts were washed with $H_2O$ and brine, dried and evaporated to give the crude product as a brown oil (1.3 g, 45%). $^1$H NMR (DMSO-$d_6$) δ1.40 (2H, m); 2.22 (2H, m); 3.30 (2H, t, J=6.6 Hz); 5.10 (1H, d, J=13.7 Hz); 5.21 (1H, d, J=13.7 Hz); 7.18 (2H, t, J=8.5 Hz); 7.59 (2H, dd, J=5.2 and 8.5 Hz); 7.78 (3H, s+d, J=8.1 Hz).

Preparation of 1-(3-Aminopropyl)-1-(4-fluorophenyl)-1,3-dihydro-5-isobenzofurancarbonitrile:

A mixture of 1-(3-azidopropyl)-1-(4-fluorophenyl)-1,3-dihydro-5-isobenzofurancaibonitrile (1.3 g, 4.4 mmol) and palladium on carbon (0.6 g, 5%) in ethanol (50 mL) was hydrogenated for 2 h. The mixture was filtered through Celite and evaporated to give the crude product as a brown oil (0.8 g, 66%). $^1$H NMR (DMSO-$d_6$) δ1.1 (1H, m); 1.22 (1H, m); 2.12 (2H, m); 2.48 (2H, t, J=7.1 Hz); 5.15 (1H, d, J=13.7 Hz); 5.19 (1H, d, J=13.7 Hz); 7.15 (2H, t, J=8.9 Hz); 7.58 (2H, dd, J=5.2 and 8.5 Hz); 7.72 (1H, d, J=8.4 Hz); 7.78 (2H, s+d, J=8.1 Hz).

Preparation of 1-[3-(N,N-Dimethylamino)propyl]-1-(4-fluorophenyl)-1,3-dihydro-5-isobenzofuran-carbonitrile, (Citalopram, Oxalate):

Sodium cyanoborohydride (0.34 g. 5.4 mmol) was added to a mixture of 1-(3-Aminopropyl)-1-(4-fluorophenyl)-1,3-dihydro-5-isobenlzofiurancarbonitrile (0.80 g, 2.7 mmol) and formaldehyde (0.44 mL, 5.4 mmol, 37% in $H_2O$) in methanol (10 mL). The resulting mixture was stirred at room temperature for 3 h, then was added more sodium cyanoborohydride (0.17 g, 2.7 mmol) and formaldehyde (0.22 mL, 2.7 mmol). After stirring at room temperature for 1 h, the mixture was quenched with H$_2$O and extracted with Et$_2$O. The organic extracts were dried and evaporated. Silica gel chromatography (EtOAc, heptane, triethylamine 75:25:1) of the residue gave the crude product, which was isolated as the oxalate salt from acetone (0.31 g, 0.8 mmol, 30%). The NMR-spectra were identical with those obtained from citalopram oxalate prepared in example 2. Anal. (C$_{20}$H$_{21}$N$_2$O, C$_2$H$_2$O$_4$, ¼ H$_2$O) calcd. C: 63.06; H: 5.67; N: 6.69. Found C: 63.28; H: 5.64; N: 6.67.

EXAMPLE 5

Preparation of 1-(4-fluorophenyl)-1-[3-(N-methylamino) propyl]-1,3-dihydro-5-isobenzofurancarbo-nitrile, Oxalate Salt:

The compound was prepared from methylamine (60 mL, 120 mmol, 2 M solution in THF) using the method described in example 3. Yield: 760 mg, 36%. $^1$H NMR (DMSO-d$_6$) δ1.40 (1H, m); 1.41 (1H, m); 2.25 (2H, t); 2.47 (3H, s); 2.83 (2H, t, J=8.0 Hz); 5.15 (1H, d, J=13.2 Hz); 5.21 (1H, d, J=13.2 Hz); 7.18 (2H, t, J=9.0 Hz); 7.59 (2H, dd, J=5.6 and 7.5 Hz); 7.73 (1H, d, J=8.1 Hz); 7.81 (3H, d +s, J=8.1 Hz).

Preparation of 1-[3-(N,N-Dimethylamino)propyl]-1-(4-fluorophenyl)-1,3-dihydro-5-isobenzo-furancarbonitrile, (Citalopram, Oxalate):

A solution of 1-[3-(N-methyl-ammonium)propyl]-1-(4-fluorophenyl)-1,3-dihydro-5-isobenzofuran-carbonitrile (0.70 g, 2.24 mmol) and formaldehyde (0.5 mL, 6.7 mmol, 37% aqueous solution) in 98% formic acid (5 mL) was refluxed for 4 h. After cooling, 4 M HCl (2 mL) was added and the resulting mixture was evaporated. 1 M NaOH (50 mL) was added to the residue and extracted with Et$_2$O (3×100 mL). The organic extract was washed with brine, dried and evaporated. The oxalate salt was isolated from acetone (0.22 g, 30%). DSC (open chamber), T$_{onset}$=157.73, T$_{peak}$=160.80. The NMR-spectra were identical with those obtained from citalopram oxalate prepared in example 2. Anal. (C$_{20}$H$_{21}$N$_2$O, C$_2$H$_2$O$_4$, ¼ H$_2$O) calcd. C: 63.06; H: 5.67; N: 6.69. Found C: 63.24; H: 5.65; N: 6.62.

What is claimed is:

1. A method for the preparation of citalopram comprising reacting a compound of formula II

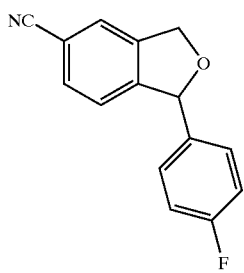

(II)

with a compound of formula

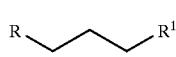

(III)

wherein R is halogen or —O—SO$_2$—X wherein X is alkyl, alkenyl, alkynyl or optionally alkyl substituted aryl or aralkyl and R$^1$ is dimethylamino, halogen, —O—SO$_2$—X wherein X is as defined above, provided that R is not halogen when R$^1$ is dimethylamino;

and if R$^1$ is dimethylamino followed by isolating citalopram base or a pharmaceutically acceptable acid addition salt thereof, and if R$^1$ is halogen or —O—SO$_2$—X wherein X is as defined above, followed by converting the resulting compound of formula

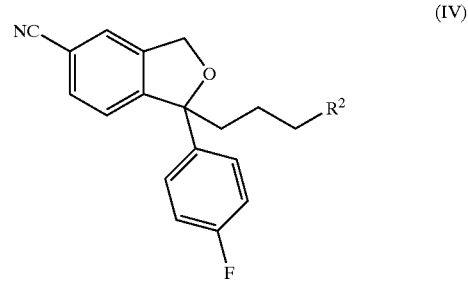

(IV)

wherein R$^2$ is halogen or a group of formula —O—SO$_2$—X wherein X is as defined above to citalopram, followed by isolating citalopram base or a pharmaceutically acceptable acid addition salt thereof.

2. A method for the preparation of citalopram according to claim 1, comprising reacting the compound of formula II with a sulphonyl ester of formula

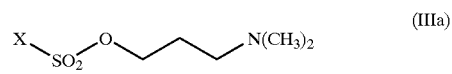

(IIIa)

wherein X is as defined in claim 1, followed by isolating citalopram base or a pharmaceutically acceptable acid addition salt thereof.

3. A method for the preparation of citalopram according to claim 1, comprising reacting a compound of formula (II) with a compound of formula

(IIIb)

wherein R and R$^2$ is as defined in claim 1, followed by reacting the resulting compound of formula (IV) with a) dimethylamine or a metal salt thereof, b) methylamine followed by reductive amination, or c) an azide followed by reduction to form the corresponding amino compound and thereafter methylation or reductive amination, to form citalopram.

4. The method according to any of claims 1–3 wherein the reaction of a compound of formula (II) with a compound of formula (III) is carried out in presence of a base selected from LDA (lithium-diisopropylamine), LiHMDS (hexamethyldisilasan lithium), NaH, NaHMDS (hexamethyldisilasan-sodium) and metalalkoxides.

5. The method according to claim 4 wherein the base is a metalkoxide selected from the group consisting of NaOMe, KOMe, LiOMe, NaOtertBu, KOtertBu and LiOtertBu.

* * * * *